United States Patent
Lee

(10) Patent No.: US 12,050,176 B2
(45) Date of Patent: Jul. 30, 2024

(54) APPARATUS AND METHOD FOR ESTIMATING BODY WATER STATUS

(71) Applicant: SAMSUNG ELECTRONICS CO., LTD., Suwon-si (KR)

(72) Inventor: June Young Lee, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 248 days.

(21) Appl. No.: 17/877,277

(22) Filed: Jul. 29, 2022

(65) Prior Publication Data

US 2023/0324293 A1  Oct. 12, 2023

(30) Foreign Application Priority Data

Apr. 12, 2022  (KR) .................. 10-2022-0045248

(51) Int. Cl.
| | | |
|---|---|---|
| *G01N 21/359* | (2014.01) | |
| *A61B 5/00* | (2006.01) | |
| *G01N 21/17* | (2006.01) | |
| *G01N 33/68* | (2006.01) | |

(52) U.S. Cl.
CPC .......... *G01N 21/359* (2013.01); *A61B 5/443* (2013.01); *G01N 21/17* (2013.01); *G01N 33/6881* (2013.01); *G01N 2021/1744* (2013.01)

(58) Field of Classification Search
CPC .. G01N 21/359; G01N 21/17; G01N 21/3554; G01N 33/6881; G01N 2021/1744; A61B 5/443; A61B 5/0075; A61B 5/681; A61B 5/1455; A61B 5/14532; A61B 5/14546; A61B 5/4845; A61B 5/7246; A61B 5/1495; A61B 5/1477; G16H 40/63
USPC .......... 356/432–440, 301–326; 600/473, 475
See application file for complete search history.

(56) References Cited

U.S. PATENT DOCUMENTS

| | | | |
|---|---|---|---|
| 6,529,767 B1 | 3/2003 | Woo et al. | |
| 6,862,534 B2 * | 3/2005 | Sterling | A61B 5/14532 702/22 |
| 10,485,472 B2 | 11/2019 | Shin et al. | |
| 11,197,632 B2 | 12/2021 | Shin et al. | |
| 2007/0292963 A1 * | 12/2007 | Dickerson | G01N 21/6486 436/164 |
| 2011/0257492 A1 * | 10/2011 | Greve | A61B 5/0075 600/306 |

(Continued)

FOREIGN PATENT DOCUMENTS

| | | |
|---|---|---|
| JP | 4872536 B2 | 2/2012 |
| KR | 10-0398362 B1 | 9/2003 |

(Continued)

*Primary Examiner* — Hoa Q Pham
(74) *Attorney, Agent, or Firm* — Sughrue Mion, PLLC

(57) ABSTRACT

An apparatus for estimating body water status includes a spectrometer having a light source configured to emit light onto an object, and a detector configured to measure a near-infrared (NIR) absorption spectrum by detecting light scattered or reflected from the object; and a processor configured to estimate an albumin concentration in the object based on the measured NIR absorption spectrum, and to estimate a body water index based on the estimated albumin concentration by using a body water index estimation model that represents a relationship between a change in the albumin concentration and a change in an amount of body water present in the object.

20 Claims, 18 Drawing Sheets

(56) References Cited

U.S. PATENT DOCUMENTS

2018/0228432 A1  8/2018  Woo et al.
2019/0167144 A1  6/2019  Jung et al.
2021/0383928 A1  12/2021  Kim et al.

FOREIGN PATENT DOCUMENTS

KR  10-2018-0015964 A  2/2018
KR  10-2021-0151525 A  12/2021

* cited by examiner

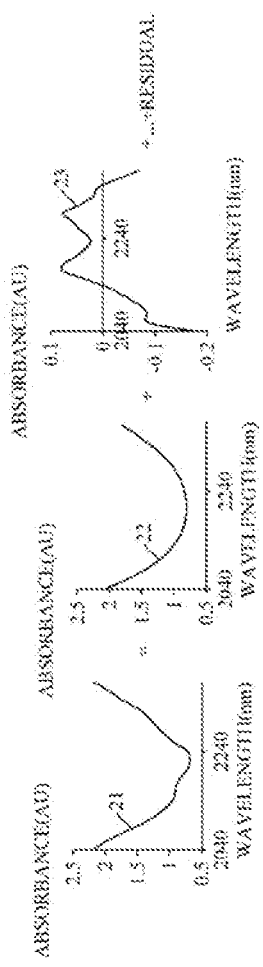

APPARATUS AND METHOD FOR ESTIMATING BODY WATER STATUS

CROSS-REFERENCE TO RELATED APPLICATION

This application is based on and claims priority under 35 U.S.C. § 119 to Korean Patent Application No. 10-2022-0045248, filed on Apr. 12, 2022, in the Korean Intellectual Property Office, the disclosure of which is incorporated herein by reference herein in its entirety.

BACKGROUND

1. Field

The disclosure relates to an apparatus and method for estimating body water status by using a spectrometer.

2. Description of the Related Art

Recently, there has been a growing interest in skin measurements using an optical method for non-invasively estimating bio-information. A light absorption method may be classified according to light wavelengths into methods of using a near-infrared wavelength, a mid-infrared wavelength, etc., and a light scattering method may be classified into methods of using elastic scattering, inelastic scattering, and the like. In the light absorption method of using the near-infrared wavelength, main bio-information content such as blood glucose, cholesterol, collagen, body water, etc., may be selectively estimated based on different absorption characteristics depending on bio-information.

As an example of the bio-information, body water is an amount of water contained in the body and accounts for about 70% of the body. If body water is insufficient, immunity may decrease or various diseases may occur due to dehydration. Accordingly, there is a need for a method of simply and accurately measuring the body water and continuously monitoring the body water.

SUMMARY

In accordance with an aspect of the disclosure, an apparatus for estimating body water status includes a spectrometer including a light source configured to emit light onto an object, and a detector configured to measure a near-infrared (NIR) absorption spectrum by detecting light scattered or reflected from the object; and a processor configured to estimate an albumin concentration in the object based on the measured NIR absorption spectrum, and to estimate a body water index based on the estimated albumin concentration by using a body water index estimation model that represents a relationship between a change in the albumin concentration and a change in an amount of body water present in the object.

The spectrometer may measure the NIR absorption spectrum by using at least one of a combination wavelength range and an overtone wavelength range.

The processor may estimate the albumin concentration by a component analysis of the NIR absorption spectrum using a Classical Least Squares (CLS) analysis.

The processor may perform the component analysis on the NIR absorption spectrum using the CLS analysis based on the Beer-Lambert Law, and estimates the albumin concentration based on an optical path length of water in the object.

The apparatus may further include an input interface configured to receive an input of weight from a user, wherein the processor estimates the body water index by applying the estimated albumin concentration and the input weight to the body water index estimation model.

The body water index may include a rate of the change in the amount of body water present in the object with respect to the input weight.

The apparatus may further include an output interface, wherein upon estimating the body water index, the processor provides a user with at least one of the albumin concentration and the body water index as a body water status diagnosis result through the output interface.

In response to the estimated body water index falling outside a predetermined threshold range, the processor may diagnose that the body water is insufficient.

In response to the processor diagnosing that the body water is insufficient, the processor may provide a user with fluid intake guidance information through an output interface.

In accordance with an aspect of the disclosure, a method of estimating body water status includes measuring a near-infrared (NIR) absorption spectrum by emitting light onto an object and detecting light scattered or reflected from the object; estimating an albumin concentration based on the measured NIR absorption spectrum; and estimating a body water index based on the estimated albumin concentration by using a body water index estimation model that represents a relationship between a change in the albumin concentration and a change in an amount of body water present in the object.

The estimating of the albumin concentration may include estimating the albumin concentration by a component analysis of the NIR absorption spectrum using a Classical Least Squares (CLS) analysis.

The estimating of the albumin concentration may include performing the component analysis on the NIR absorption spectrum using the CLS analysis based on the Beer-Lambert Law, and estimating the albumin concentration based on an optical path length of water in the object.

The estimating of the body water index may include estimating the body water index by applying the estimated albumin concentration and a weight to the body water index estimation model, the weight being input by a user through an input interface.

The body water index may include a rate of the change in the amount of body water present in the object with respect to the input weight.

In accordance with an aspect of the disclosure, an electronic device includes a memory for storing computer-readable instructions; and a processor for estimating a body water index by executing the instructions, wherein the processor estimates an albumin concentration based on a spectrum of an object, and estimates the body water index based on the estimated albumin concentration by using a body water index estimation model that represents a relationship between a change in the albumin concentration and a change in an amount of body water present in the object.

The processor may perform a component analysis on the spectrum using a Classical Least Squares (CLS) analysis based on the Beer-Lambert Law, and estimate the albumin concentration based on an optical path length of water in the object.

The processor may estimate the body water index by applying the estimated albumin concentration and a user's weight to the body water index estimation model.

In accordance with an aspect of the disclosure, an electronic device includes a main body, and an apparatus for estimating body water status which is disposed in the main body, wherein the apparatus for estimating the body water status includes a spectrometer including a light source configured to emit light onto an object, and a detector configured to measure a near-infrared (NIR) absorption spectrum by detecting light scattered or reflected from the object; and a processor configured to estimate an albumin concentration in the object based on the measured NIR absorption spectrum, and to estimate a body water index based on the estimated albumin concentration by using a body water index estimation model that represents a relationship between a change in the albumin concentration and a change in an amount of body water present in the object.

The processor may perform a component analysis on the NIR absorption spectrum using a Classical Least Squares (CLS) analysis based on the Beer-Lambert Law, and estimate the albumin concentration based on an optical path length of water in the object.

The electronic device may include at least one of a smart watch, a smart band, smart glasses, a smart necklace, and an ear-type device.

BRIEF DESCRIPTION OF THE DRAWINGS

FIGS. 2A and 2B are diagrams illustrating an example of CLS fitting of an NIR absorption spectrum in a combination wavelength range and an overtone wavelength range.

Figure 1:
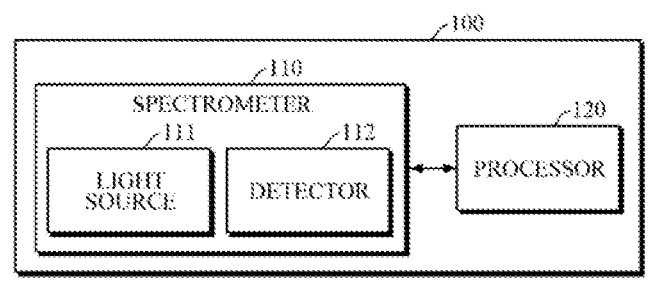
FIG. 1 is a block diagram illustrating an apparatus for estimating body water status according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Hereinafter, embodiments of an apparatus and method for estimating body water status will be described in detail with reference to the accompanying drawings.

FIG. 1 is a block diagram illustrating an apparatus for estimating body water status according to an embodiment of the disclosure. An apparatus 100 for estimating body water status may be mounted in a wearable device worn by a user. In this case, the wearable device may be formed in various types, such as a wristwatch-type wearable device, a bracelet-type wearable device, a wristband-type wearable device, a ring-type wearable device, a necklace-type wearable device, a glasses-type wearable device, a headband-type wearable device, an earbud-type wearable device, a shoes-type wearable device, an earrings-type wearable device, etc., but the wearable device is not specifically limited to the type or size.

Referring to FIG. 1, the apparatus 100 for estimating body water status includes a spectrometer 110 and a processor 120.

The spectrometer 110 may measure a spectrum from an object. In this case, various spectrometers, such as a laser spectrometer, a near-infrared spectrometer, a mid-infrared spectrometer, a Raman spectrometer, etc., may be used as the spectrometer 110. For convenience of explanation, the following description will be given using a near-infrared spectrometer as an example. The object may be a user's skin, e.g., an upper part of the wrist where veins or capillaries are located or the skin surface of the wrist that is adjacent to the radial artery, or peripheral parts of the body, such as fingers, toes, earlobes, and the like where blood vessels are densely distributed. However, the object is not limited thereto.

The spectrometer 110, for example, the near-infrared spectrometer, may include a light source 111 and a detector 112.

The light source 111 may emit light onto an object, and the detector 112 may detect an optical signal by receiving light scattered or reflected from the object. The light source 111 may be formed as a light emitting diode (LED), a laser diode (LD), a phosphor, etc., and may emit light in a near-infrared range. Once the light source 111 emits light onto the user's skin, which is the object, according to a control signal of the processor 120, the emitted light may penetrate through the user's skin into body tissue, and after reaching the body tissue, the light may be scattered or reflected from the user's body tissue to return through the user's skin.

The detector 112 may measure a spectrum by detecting the light that returns through the user's skin. In this case, the detector 112 may include a photodiode, a photodiode array, a photo transistor (PTr), and the like. However, the detector 112 is not limited thereto, and may include a complementary metal-oxide semiconductor (CMOS) image sensor, a charge-coupled device (CCD) image sensor, and the like.

In response to input of measurement conditions, the spectrometer 110 may measure a spectrum from the object. For example, the spectrometer 110 may measure a near-infrared (NIR) absorption spectrum by detecting light scattered or reflected from the object under the measurement conditions. Here, the measurement conditions may include an optical path length, a light source intensity for each wavelength, or detector noise characteristics for each wavelength, but are not limited thereto. For example, the optical path length may vary depending on optical coefficients, such as scattering, absorption, and anisotropy of skin, etc., which are characteristics of the object to be measured, and the light source intensity for each wavelength or the detector noise characteristics for each wavelength may be changed due to a change in device characteristics of a spectrometer. Accordingly, by reflecting these data as measurement conditions, the spectrum may be measured from the object.

In addition, the spectrometer 110 may measure the NIR absorption spectrum by using at least one of a combination wavelength range or an overtone wavelength range. For example, the combination wavelength range corresponds to a wavelength range from 2040 nm to 2380 nm, and the overtone wavelength range corresponds to a wavelength range from 1540 nm to 1820 nm, and the two wavelength ranges are mainly used as wavelength ranges for the spectrometer. By limiting the wavelength ranges, precise measurements may be provided compared to measurements in a comparatively wide wavelength range.

The processor 120 may be electrically connected to the spectrometer 110 and may control the spectrometer 110. In response to a user's request, the processor 120 may control the spectrometer 110 such that the processor 120 receives the measured NIR absorption spectrum from the spectrometer 110. In addition, the processor 120 may estimate a user's body water status based on the received NIR absorption spectrum.

Body water is generally measured using an impedance method, but a short-term change in body water status or a sensitive change in body water of 1 liter or less may not be measured accurately by using the impedance method. In addition, when body water is measured using plasma osmotic concentration or urine osmolality or specific gravity, it is required to take a blood and urine sample, and a separate chemical analysis process is required, such that the measurement may not be performed easily. Meanwhile, the body water has a correlation with albumin concentration. That is, if body water decreases, water in plasma decreases, thereby leading to a relative increase in albumin concentration. By measuring the albumin concentration based on the correlation, a user's body water status may be estimated. In this case, the albumin concentration may be obtained by using a spectrum, and thus, by using a simple spectrometer, the user's body water status may be estimated in a non-invasive and convenient manner.

For example, by estimating the albumin concentration based on the NIR absorption spectrum received from the spectrometer 110, and estimating a body water index based on the estimated albumin concentration, the processor 120 may estimate the user's body water status.

First, the processor 120 may estimate the albumin concentration by component analysis of the spectrum using a classical least squares (CLS) analysis. For example, for the received NIR absorption spectrum, the processor 120 may perform component analysis on a pure spectrum, such as water, albumin, etc., using classical least squares (CLS) analysis based on the Beer-Lambert Law according to Equation 1, and may estimate the albumin concentration based on an optical path length of water in the object (e.g., the user's skin).

$$\text{NIR Spectrum} = \mu_a \cdot C_w \cdot L + \mu_o \cdot C_o \cdot L + \ldots + C_o \cdot \text{offset} + C_s \cdot \text{slope} + R \quad \text{[Equation 1]}$$

Herein, $\mu_w$ denotes an absorption coefficient of water; Cw denotes a water concentration; L denotes the optical path length of water; $\mu_a$ denotes an absorption coefficient of albumin; Ca denotes an albumin concentration; offset denotes an environment change correction component; Co denotes a concentration of the offset; slope denotes a temperature change correction component; Cs denotes a concentration of the slope; and R denotes a residual. In this case, the absorption coefficient of water, water concentration, absorption coefficient of albumin, environment change correction component and concentration thereof, temperature change correction component and concentration thereof, and residual may be predetermined values. Generally, water contained in the skin is the main component of skin as water accounts for 70% of the skin, and thus, it can be assumed that an optical path length of water, which has passed through a pure water component is similar to an optical path length having passed through the skin. That is, a known absorption coefficient of albumin $\mu_a$ and optical path length L of water may be applied to the spectrum component of albumin in Equation 1, and a final albumin concentration Ca may be obtained by Equation 1.

Figure 2B:
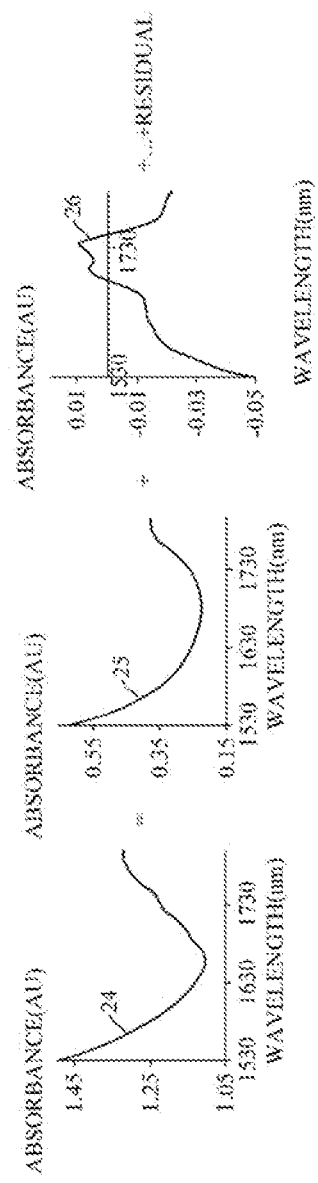

FIGS. 2A and 2B are diagrams illustrating Equation 1 shown in graphs and CLS fitting of an NIR absorption spectrum in each of a combination wavelength range and an overtone wavelength range.

In FIG. 2A, an NIR spectrum 21 measured in the combination wavelength range may be represented by a sum of a water spectrum 22, corresponding to principal spectra $\mu_w \cdot Cw \cdot L$, and an albumin spectrum 23 corresponding to $\mu_a \cdot Ca \cdot L$, and the like. Further, in FIG. 2B, an NIR spectrum 24 measured in the overtone wavelength range may be represented by a sum of a water spectrum 25, corresponding to principal spectra $\mu_w \cdot Cw \cdot L$, and an albumin spectrum 26 corresponding to $\mu_a \cdot Ca \cdot L$, and the like.

Then, the processor 120 may estimate a body water index by applying the estimated albumin spectrum. For example, the processor 120 may estimate the body water index based on the estimated albumin spectrum by using a body water index estimation model which represents a relationship between the albumin concentration or a variation in albumin concentration and a change in body water. In this case, the body water index may indicate an increase or decrease in body water with respect to a user's weight. Accordingly, by inputting a user's weight and the estimated albumin concentration to the body water index estimation model, the processor 120 may estimate, as the body water index, a rate of change in body water with respect to weight. However, the body water index is not limited thereto. In this case, the body water index estimation model may be defined as various linear or non-linear combination functions, such as addition, subtraction, division, multiplication, logarithm value, regression equation, and the like, with no specific limitation.

For example, if a user's weight is 70 kg and the estimated albumin concentration increases by 2.6% to 2.976 g/dl from a normal state concentration, e.g., 2.9 g/dl, the processor 120 may obtain current body water of 13.65 liters, showing a decrease by 0.35 liters from normal body water of 14 liters for 70 kg body weight, by using the body water estimation model. Based on the result, the processor 120 may obtain 0.5% (0.35/70*100), which is a rate of change in body water with respect to weight, as the body water index.

Upon estimating the body water index, the processor 120 may diagnose a user's current body water status based on the estimated body water index. For example, if the body water index falls outside a predetermined threshold value, the processor 120 may diagnose that the user's current body water status is not normal, e.g., body water is insufficient. For example, in the above example, if a rate of change (e.g., decreasing amount) in body water with respect to the user's weight is 0.5%, and if the predetermined threshold is 0.4%, the processor 120 may determine that the user's body water is insufficient.

In an embodiment, the processor 120 may measure a relative amount with respect to a change in body water according to a change in albumin concentration by using the body water index estimation model. Based on the measurement, even when the optical path length of water is changed due to background noise, e.g., pressure, temperature, and the like during measurement, the albumin concentration may be calculated according to a changed optical path length of water, and even when there is the background noise, accurate measurement may be performed.

Upon estimating the body water index, the processor 120 may provide a user with the albumin concentration and/or body water index as a body water status diagnosis result, and if the body water is insufficient based on the body water status diagnosis result, the processor 120 may provide the user with fluid intake guidance information.

FIGS. 3A to 3F are diagrams explaining an example of providing a body water status diagnosis result and/or fluid intake guidance information by using a smart watch.

Figure 3A:
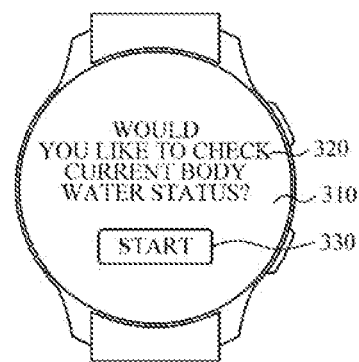
FIGS. 3A to 3F are diagrams explaining an example of providing a body water status diagnosis result and/or fluid intake guidance information by using a smart watch.
Figure 3B:
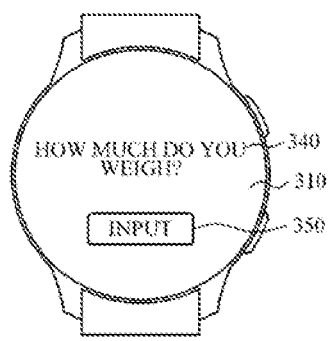

Referring to FIGS. 3A and 3B, the processor 120 may display a start text message on a display device 310 of an output interface. For example, as illustrated herein, the processor 120 may display a text message 320, such as "WOULD YOU LIKE TO CHECK CURRENT BODY WATER STATUS?", on the display device 310 for providing a user with body water status information.

If the user touches the start button 330 in FIG. 3A, the processor 120 may display a text message, recommending the user to input the user's personal information, on the display device 310 as illustrated in FIG. 3B. For example, the processor 120 may display a text message 340 regarding the user's physical information, such as "How much do you weigh?", on the display device, and the user may input the answer by touching an "input" button 350. As described above, in addition to the case where the user directly inputs the information, if the user's physical information is already stored in an electronic device, or if the processor 120 is connected to another health application or is connected to another device (e.g., medical institution server) such that the processor 120 may obtain the user's physical information, the operation illustrated in FIG. 3B may be omitted.

Figure 3C:
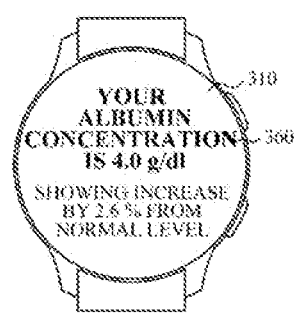
Figure 3D:
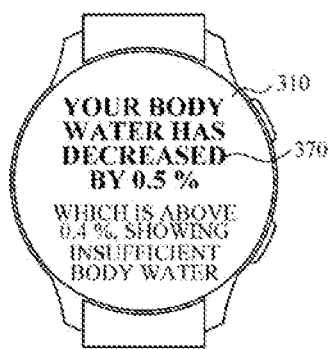

FIGS. 3C and 3D are diagrams illustrating a text message regarding a body water status diagnosis result displayed on the display device 310 according to an embodiment of the disclosure.

Referring to FIGS. 3C and 3D, if the estimated albumin concentration is 4.0 g/dl, for example, the processor 120 may output a text message 360, such as "YOUR ALBUMIN CONCENTRATION IS 4.0 g/dl, SHOWING INCREASE BY 2.6% FROM NORMAL LEVEL" through the display device 310. In addition, upon estimating the body water index of 0.5% based on the estimated albumin concentration, the processor 120 may output a text message 370, such as "YOUR BODY WATER HAS DECREASED BY 0.5% WHICH IS ABOVE 0.4%, SHOWING INSUFFICIENT BODY WATER" through the display device 310.

Figure 3E:
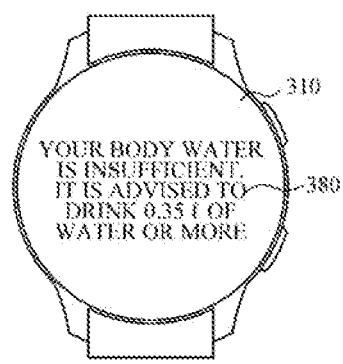
Figure 3F:

FIGS. 3E to 3F are diagrams illustrating a final text message regarding fluid intake guidance information displayed on the display device 310 according to an embodiment of the disclosure.

Referring to FIGS. 3E to 3F, if body water is insufficient based on, for example, a body water status diagnosis result, the processor 120 may output a text message 380, such as "YOUR BODY WATER IS INSUFFICIENT. IT IS ADVISED TO DRINK 0.35 L OF WATER OR MORE" through the display device 310. For example, the processor 120 may output a text 390, such as "0.35 L OF WATER OR MORE" along with fluid intake guidance information in a visual graphic form. In this case, the visual graphic may be displayed using a bar graph, water drop-shaped figure, and the like, but the display is not limited thereto.

In addition, the processor 120 may also output the body water status diagnosis result and/or fluid intake guidance information as a voice message, and may output both the text message and the voice message at the same time. Further, the processor 120 may also output a warning alarm for insufficient body water and fluid intake through an output interface.

Figure 4:
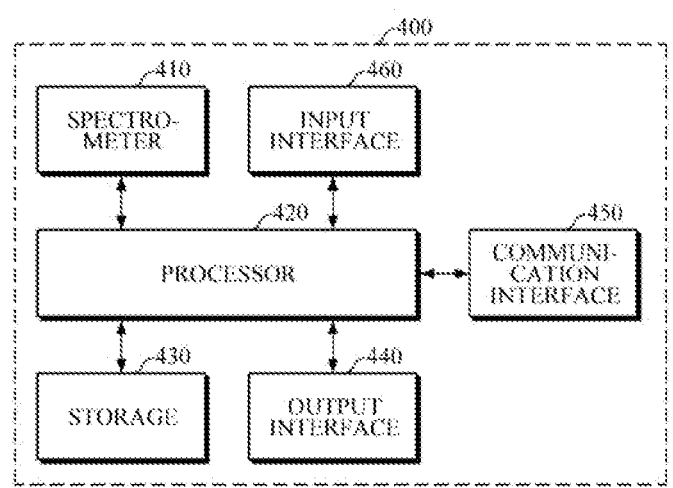
FIG. 4 is a block diagram illustrating an apparatus for estimating body water status according to an embodiment.

FIG. 4 is a block diagram illustrating an apparatus for estimating body water status according to an embodiment of the disclosure.

Referring to FIG. 4, an apparatus 400 for estimating body water status may include a spectrometer 410, a processor 420, a storage 430, an output interface 440, a communicator 450, and an input interface 460. In this case, the spectrometer 410 and the processor 420 are the same as the spectrometer 110 and the processor 120 in the embodiment of FIG. 1, such that a detailed description thereof will be omitted.

The storage 430 may store information related to estimating body water status. For example, the storage 430 may store the optical path length of water, albumin concentration, body water status estimation model, and the like.

The storage 430 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 440 may provide processing results of the processor 420 to a user. For example, the output interface 440 may provide the albumin concentration, body water index, and/or fluid intake guidance information of the processor 420 through the display. In this case, along with or without the visual display, the output interface 440 may provide the user with the information in a non-visual manner by voice, vibrations, tactile sensation, and the like using an audio output module, such as a speaker, or a haptic module and the like.

The communication interface 450 may communicate with an external device to transmit and receive various data related to estimating body water status. The external device may include an information processing device such as a smartphone, a tablet PC, a desktop computer, a laptop computer, and the like. For example, the communication interface 450 may transmit a body water status estimation result to the external device, such as a user's smartphone and the like, so that the user may manage and monitor analysis results using a device having a relatively high performance.

The communication interface 450 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, these are merely examples and are not intended to be limiting.

The input interface 460 may receive bio-information from the user. For example, the processor 420 may provide the user with an interface through the input interface 460, and may estimate the body water index by applying the user's weight, input through the interface, and the estimated albumin concentration to a body water index estimation model.

Figure 5:
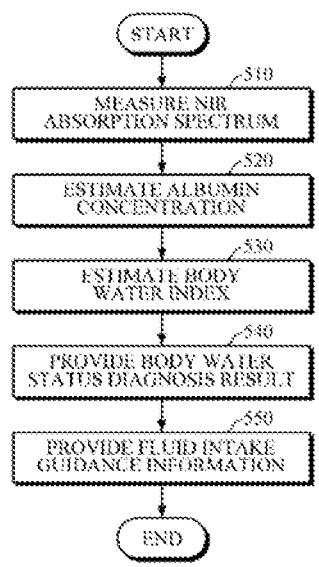
FIG. 5 is a flowchart illustrating a method of estimating body water status according to an embodiment.

FIG. 5 is a flowchart illustrating a method of estimating body water status according to an embodiment of the disclosure.

The method of FIG. 5 may be an example of a method of estimating body water status performed by the apparatuses 100 and 400 for estimating body water status according to the embodiments of FIGS. 1 and 4, which are described in detail above, and thus will be briefly described below in order to avoid redundancy.

Referring to FIG. 5, the apparatus for estimating body water status may first measure an NIR absorption spectrum in 510 by emitting light onto an object and detecting light scattered or reflected from the object.

Then, the apparatus for estimating body water status may estimate an albumin concentration based on the measured spectrum in 520. In this case, the apparatus for estimating body water status may estimate the albumin concentration by component analysis of the spectrum using CLS component analysis. For example, the apparatus for estimating body water status may perform component analysis on the spectrum using CLS analysis based on the Beer-Lambert Law and may estimate the albumin concentration based on an optical path length of water in the object.

Subsequently, the apparatus for estimating body water status may estimate a body water index based on the estimated albumin concentration by using a body water index estimation model that represents a relationship between a change in albumin concentration and a change in body water in 530. For example, the apparatus for estimating body water status may estimate the body water index by applying the estimated albumin concentration and a user's weight, input by the user through the input interface, to the body water index estimation model. In this case, the body water index indicates a rate of change in body water with respect to weight.

Next, the apparatus for estimating body water status may provide a body water status diagnosis result to the user in 540. For example, the apparatus for estimating body water status may provide the user with the albumin concentration and/or the body water index as the body water status diagnosis result. In addition, if the estimated body water index falls outside a predetermined threshold range, the apparatus for estimating a body water status may diagnose that body water is insufficient.

Then, the apparatus for estimating body water status may provide fluid intake guidance information to the user in 550. For example, with or without a visual display, the apparatus for estimating body water status may provide the fluid intake guidance information, such as an amount of fluid required or recommended for the user, in a non-visual manner by voice, vibrations, tactile sensation, and the like using an audio output module, such as a speaker, or a haptic module, and the like.

FIGS. 6 to 10 are diagrams illustrating structures of electronic devices including an apparatus for estimating body water status. Examples of the electronic devices may include not only a smartphone, but also wearables devices such as a smartwatch, a smart band, smart glasses, a smart necklace, a smart ring, an earrings-type wearable device, a shoes-type wearable device, and an ear-wearable device, but the electronic devices are not limited thereto.

Figure 6:
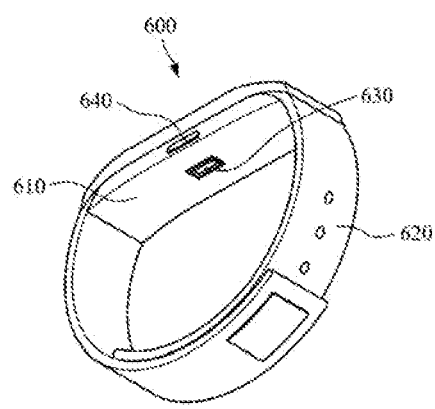
FIGS. 6-8, 9A-9C, and 10 are diagrams illustrating structures of electronic devices including an apparatus for estimating body water status.

Referring to FIG. 6, an electronic device may be implemented as a smartwatch wearable device 600 and may include a main body 610 and a wrist strap 620.

The main body 610 may have various shapes. A battery for supplying power to various modules of the device 600 may be embedded in the main body 610 and/or the strap 620. The strap 620 may be connected to both ends of the main body 610 to allow the main body to be worn on a user's wrist, and may be flexible so as to be wrapped around the user's wrist. The strap 620 may be composed of a first strap and a second strap which are separate from each other. An end of the first strap and an end of the second strap are connected to respective sides of the main body 610, and the other ends thereof may be fastened to each other via a fastening means. In this case, the fastening means may be formed as magnetic fastening, Velcro fastening, pin fastening, etc., but is not limited thereto. Further, the strap 620 is not limited thereto, and may be integrally formed as a non-detachable band.

The main body 610 may include an apparatus for estimating body water status. A spectrometer 630, a processor, an output interface, a storage, a communication interface, and an input interface may be mounted in the apparatus for estimating body water status. However, depending on the size and shape of a form factor and the like, some of the storage and the communication interface may be omitted. Once an NIR absorption spectrum is measured by the spectrometer 630, the processor may estimate an albumin concentration based on the measured spectrum and may estimate a body water index based on the estimated albumin concentration. For example, the processor may perform component analysis on the spectrum using CLS analysis based on the Beer-Lambert Law, and may estimate the albumin concentration based on an optical path length of water. In addition, the processor may estimate the body water index by applying the estimated albumin concentration and a user's weight, input by the user through the input interface, to a predetermined body water index estimation model. For example, upon estimating the body water index, the processor may provide the user with at least one of the albumin concentration and the body water index as a body water status diagnosis result through the output interface. In addition, if the estimated body water index falls outside a predetermined threshold value, the processor may diagnose that body water is insufficient and may provide fluid intake guidance information to the user through the output interface. In this case, the body water index may indicate a rate of change in body water with respect to weight. However, the body water index is not limited thereto.

Referring back to FIG. 6, a manipulator 640 may be formed on a side surface of the main body 610 as illustrated herein. The manipulator 640 may receive a user's command and may transmit the received command to the processor. In addition, the manipulator 640 may have a power button to turn on/off the wearable device 600. A display may be provided on a front surface of the main body 610 and may display various application screens, including a body water status diagnosis result, time information, fluid intake guidance information, and the like.

Figure 7:
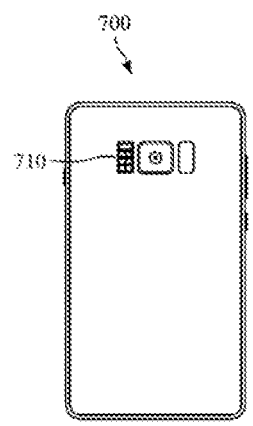

Referring to FIG. 7, an electronic device 700 may be implemented as a mobile device 700 such as a smartphone.

The mobile device 700 may include a housing and a display panel. The housing may form the exterior of the mobile device 700. The housing has a first surface, on which a display panel and a cover glass may be disposed sequentially, and the display panel may be exposed to the outside through the cover glass. A spectrometer 710, a camera module and/or an infrared sensor, and the like may be disposed on a second surface of the housing. The spectrometer 710 may include one or more light sources and detectors. The spectrometer 710 may be mounted on the second surface, but is not limited thereto and may be formed in combination with a fingerprint sensor or a touch panel formed on the first surface of the housing. When a user transmits a request for estimating body water status by executing an application and the like installed in the mobile device 700, the mobile device 700 may estimate body water status by using the spectrometer 710 and the processor in the mobile device 700, and may provide the body water status diagnosis result and/or fluid intake guidance information as images and/or sounds to the user.

Figure 8:
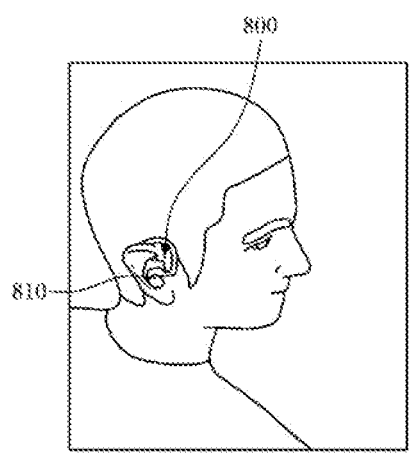

Referring to FIG. 8, an electronic device 800 may be implemented as an ear-wearable device 800.

The ear-wearable device 800 may include a main body and an ear strap. A user may wear the ear-wearable device 800 by hanging the ear strap on the user's auricle. The ear strap may be omitted depending on a shape of the ear-wearable device 800. The main body may be inserted into the external auditory meatus. A spectrometer 810 may be mounted in the main body. Further, the ear-wearable device 800 may provide the user with a body water status estimation result as sound, or may transmit the estimation result to an external device, e.g., a mobile device, a tablet PC, etc., through a communication module provided in the main body.

Figure 9A:
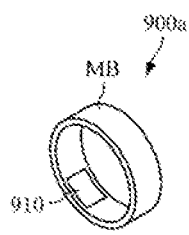
Figure 9B:
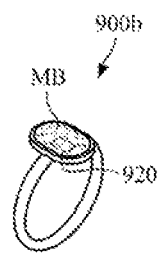
Figure 9C:
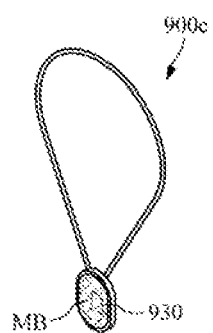

Referring to FIGS. 9A to 9C, an electronic device may be implemented as a bracelet-type wearable device 900a as shown in FIG. 9A, a ring-type wearable device 900b as shown in FIG. 9B, or a necklace-type wearable device 900c as shown in FIG. 9C. Each of the bracelet-type wearable device 900a, the ring-type wearable device 900b, and the necklace-type wearable device 900c may include a main body MB and spectrometers 910, 920, and 930, respectively, and a processor included in the main body MB may estimate an albumin concentration based on a spectrum obtained from the spectrometers 910, 920, and 930, and may estimate a body water index by using a body water index estimation model based on the estimated albumin concentration. In this case, the estimated body water index may be transmitted to an external device, such as a wristwatch-type wearable device or a smartphone, to be provided to a user through a display.

Figure 10:
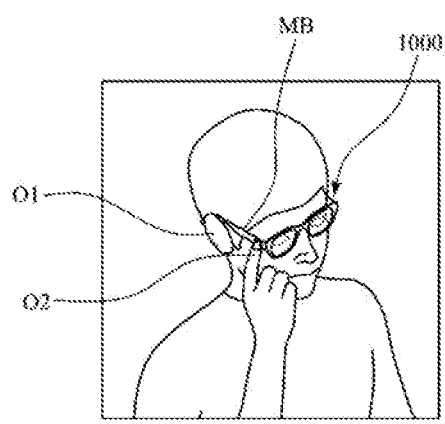

Referring to FIG. 10, the electronic device may be a smart glasses 1000 type wearable device. A spectrometer may be disposed in various areas of a main body MB that comes into contact with various body parts, such as the bridge of the nose, a portion near the ears 01, a finger 02, etc., so as to measure a spectrum from the various body parts while a user wears the glasses. A processor may be included in the main body MB to estimate a body water index, and may transmit an estimation result to an external device so that the estimation result may be provided to the user through a display, or a display may be directly installed on lenses of the glasses such that the user may directly check the estimation result through the glasses.

In an embodiment, the electronic device may include a memory for storing various computer-readable instructions and a processor for estimating a body water index by executing the instructions. For example, the processor may estimate an albumin concentration based on an object's spectrum and may estimate a body water index based on the estimated albumin concentration by using a body water index estimation model that represents a relationship between a change in albumin concentration and a change in body water. In this case, the processor may receive the object's spectrum from an external device through a communication interface, in which case the electronic device may not include a separate spectrometer.

The disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing embodiments of the disclosure can be readily deduced by programmers of ordinal), skill in the art to which the disclosure pertains.

The disclosure has been described herein with regard to embodiments. However, it will be obvious to those skilled in the art that various changes and modifications can be made without changing technical conception and essential features of the disclosure. Thus, it is clear that the above-described embodiments are illustrative in all aspects and are not intended to limit the disclosure.

What is claimed is:

1. An apparatus for estimating body water status, the apparatus comprising:
   a spectrometer comprising a light source configured to emit light onto an object, and a detector configured to measure a near-infrared (NIR) absorption spectrum by detecting light scattered or reflected from the object; and
   a processor configured to estimate an albumin concentration in the object based on the measured NIR absorption spectrum, and to estimate a body water index based on the estimated albumin concentration by using a body water index estimation model that represents a relationship between a change in the albumin concentration and a change in an amount of body water present in the object.

2. The apparatus of claim 1, wherein the spectrometer measures the NIR absorption spectrum by using at least one of a combination wavelength range and an overtone wavelength range.

3. The apparatus of claim 1, wherein the processor estimates the albumin concentration by a component analysis of the NIR absorption spectrum using a Classical Least Squares (CLS) analysis.

4. The apparatus of claim 3, wherein the processor performs the component analysis on the NIR absorption spectrum using the CLS analysis based on the Beer-Lambert Law, and estimates the albumin concentration based on an optical path length of water in the object.

5. The apparatus of claim 1, further comprising an input interface configured to receive an input of weight from a user,
   wherein the processor estimates the body water index by applying the estimated albumin concentration and the input weight to the body water index estimation model.

6. The apparatus of claim 5, wherein the body water index comprises a rate of the change in the amount of body water present in the object with respect to the input weight.

7. The apparatus of claim 1, further comprising an output interface,
wherein upon estimating the body water index, the processor provides a user with at least one of the albumin concentration and the body water index as a body water status diagnosis result through the output interface.

8. The apparatus of claim 1, wherein in response to the estimated body water index falling outside a predetermined threshold range, the processor diagnoses that the body water is insufficient.

9. The apparatus of claim 8, wherein in response to the processor diagnosing that the body water is insufficient, the processor provides a user with fluid intake guidance information through an output interface.

10. A method of estimating body water status, the method comprising:
measuring a near-infrared (NIR) absorption spectrum by emitting light onto an object and detecting light scattered or reflected from the object;
estimating an albumin concentration based on the measured NIR absorption spectrum; and
estimating a body water index based on the estimated albumin concentration by using a body water index estimation model that represents a relationship between a change in the albumin concentration and a change in an amount of body water present in the object.

11. The method of claim 10, wherein the estimating of the albumin concentration comprises estimating the albumin concentration by a component analysis of the NIR absorption spectrum using a Classical Least Squares (CLS) analysis.

12. The method of claim 11, wherein the estimating of the albumin concentration comprises performing the component analysis on the NIR absorption spectrum using the CLS analysis based on the Beer-Lambert Law, and estimating the albumin concentration based on an optical path length of water in the object.

13. The method of claim 10, wherein the estimating of the body water index comprises estimating the body water index by applying the estimated albumin concentration and a weight to the body water index estimation model, the weight being input by a user through an input interface.

14. The method of claim 13, wherein the body water index comprises a rate of the change in the amount of body water present in the object with respect to the input weight.

15. An electronic device comprising:
a memory for storing computer-readable instructions; and
a processor for estimating a body water index by executing the instructions,
wherein the processor estimates an albumin concentration based on a spectrum of an object, and estimates the body water index based on the estimated albumin concentration by using a body water index estimation model that represents a relationship between a change in the albumin concentration and a change in an amount of body water present in the object.

16. The electronic device of claim 15, wherein the processor performs a component analysis on the spectrum using a Classical Least Squares (CLS) analysis based on the Beer-Lambert Law, and estimates the albumin concentration based on an optical path length of water in the object.

17. The electronic device of claim 15, wherein the processor estimates the body water index by applying the estimated albumin concentration and a user's weight to the body water index estimation model.

18. An electronic device comprising a main body, and an apparatus for estimating body water status which is disposed in the main body,
wherein the apparatus for estimating the body water status comprises:
a spectrometer comprising a light source configured to emit light onto an object, and a detector configured to measure a near-infrared (NIR) absorption spectrum by detecting light scattered or reflected from the object; and
a processor configured to estimate an albumin concentration in the object based on the measured NIR absorption spectrum, and to estimate a body water index based on the estimated albumin concentration by using a body water index estimation model that represents a relationship between a change in the albumin concentration and a change in an amount of body water present in the object.

19. The electronic device of claim 18, wherein the processor performs a component analysis on the NIR absorption spectrum using a Classical Least Squares (CLS) analysis based on the Beer-Lambert Law, and estimates the albumin concentration based on an optical path length of water in the object.

20. The electronic device of claim 18, wherein the electronic device comprises at least one of a smart watch, a smart band, smart glasses, a smart necklace, and an ear-type device.

* * * * *